US00PP08204P

United States Patent [19]

Veldhuyzen Van Zanten

[11] Patent Number: Plant 8,204

[45] Date of Patent: Apr. 13, 1993

[54] ALSTROEMERIA NAMED VICTORIA

[75] Inventor: G. E. Veldhuyzen Van Zanten, Hillegon, Netherlands

[73] Assignee: Gebr. van Zanten, Hillegom, Netherlands

[21] Appl. No.: 800,216

[22] Filed: Nov. 29, 1991

[51] Int. Cl.[5] ..... A01H 5/00
[52] U.S. Cl. ..... Plt./87.2
[58] Field of Search ..... Plt./87.1

[56] References Cited

U.S. PATENT DOCUMENTS

P.P. 6,035 10/1987 van Andel ..... Plt. 87.1

*Primary Examiner*—James R. Feyrer
*Attorney, Agent, or Firm*—Tilton, Fallon, Lungmus & Chestnut

[57] ABSTRACT

A new and distinct variety of Alstroemeria characterized by its profuse production of medium sized flowers the outer petals of which are burnt orange in color, and the inner petals are mainly light yellow in color marked end to end with dark brown longitudinal pencil stripes, the plant itself having a vigorous upright growth habit with long stems and a more or less continuous production of flowers during each of its recurrent blooming seasons.

1 Drawing Sheet

BACKGROUND OF THE NEW PLANT

This new variety of Alstroemeria originated as a seedling produced by my crossing of unnamed plants selected from my breeding stock maintained at Hillegon, The Netherlands, for development purposes, this particular seedling having been selected by me for propagation because of the very unusual color and pattern of its blossoms and its profuse production of medium sized flowers.

This new plant is the result of breeding efforts carried on by me at Hillgon, The Netherlands since 1985, with the object of producing new types of alstroemeria plants and the selected seedling was propagated by me and under my direction by root division at Hillegon and successive generations of this plant have demonstrated that the distinctive characteristics of the parent hybrid hold true from generation to generation and appear to be firmly fixed. Propagation of this new variety is now being carried on at Aalsmeer by root stock division.

DESCRIPTION OF THE DRAWING

My new Alstroemeria plant is illustrated by the accompanying photographic drawing which, in full color, shows the distinguishing color characteristics and flower form of this plant, the color rendition being as nearly true as it is reasonably possible to obtain by conventional professional procedures.

Description of the New Plant

The following is a detail description of my new Alstroemeria plant with color designations according to The R.H.S. Colour Chart of The Royal Horticultural Society of London, England.

THE PLANT

Origin: Seedling.
Parentage:
- *Seed parent.*—Unnamed and unpatented breeding stock.
- *Pollen parent.*—Unnamed and unpatented breeding stock.

Classification:

- *Botanic.*—Alstroemeria Hybrid.
- *Commercial.*—Alstroemeria.

Form: Bush having tall, slender flowering stems with flowr bearing branches of simple umbel form at their tops.
Height: From 120 to 180 cm.
Cane length: From 120 to 180 cm.
Growth: Strong and upright.
Foliage:
- *Quantity.*—Medium.
- *Number of leaves.*—15 to 25 leaves per stem, varying ascending to season of growth.
- *Size of leaf.*—Long, about 14 cm.
- *Leaf shape.*—Elliptic.
- *Texture.*—Glossy.
- *Color.*—Upper side — Dark green. Under side — Medium green.

Rhizomes:
- *Size.*—About 5 to 10 cm.
- *Color.*—Pale White.

THE BUD

Form: Long.
Size:
- *Diameter.*—About 1.5 cm.
- *Length.*—About 4 cm.

Rate of opening: Normal.
Calyx: No calyx.
Peduncle:
- *Length.*—Long.
- *Color.*—Green with anthocyane.

THE FLOWER

Blooming habit: Continuous the year around.
Flower size: Medium.
- *Diameter.*—6 cm.
- *Depth.*—5 cm.

Borne: In umble cluster.
Shape: When bloom first opens, cup-shaped. When bloom matures, cup-shaped.
Petalage:
- *Number of petals.*—6.
- *Form.*—Broad oval.
- *Texture.*—Leathery.

*Appearance.*—Satiny.

*Color.*—Outer petals — 31-B. Inside petals — 12-A.

Peduncle:

*Length.*—Medium/High.

*Color.*—Medium green.

Persistence: The petals hold on the flower stem for about 10 days.

Lasting quality:

*On the plant.*—Very good.

*As cut flower.*—Very good.

THE REPRODUCTIVE ORGANS

Stamens:

*Number.*—6.

*Anthers.*—Size: About 0.5 mm. Color: Light red brown.

*Filaments.*—Length: About 4 cm. Color: Light red brown.

Pistils:

*Number.*—One.

Style: About 3 cm. long.

*Color.*—Orange red.

*Stigma.*—Color: Orange.

FRUIT

Fertility: The fruit is sterile.

Shape: Ovoid.

Color at maturity: Light brown.

I claim:

1. The new and distinct variety of Alstroemeria plant substantially as herein shown and described, characterized by the distinctive burnt orange coloring of the flowers and the yellow coloring at the base of the inside petals, and by the longitudinal pencil stripes on the inside petals.

* * * * *

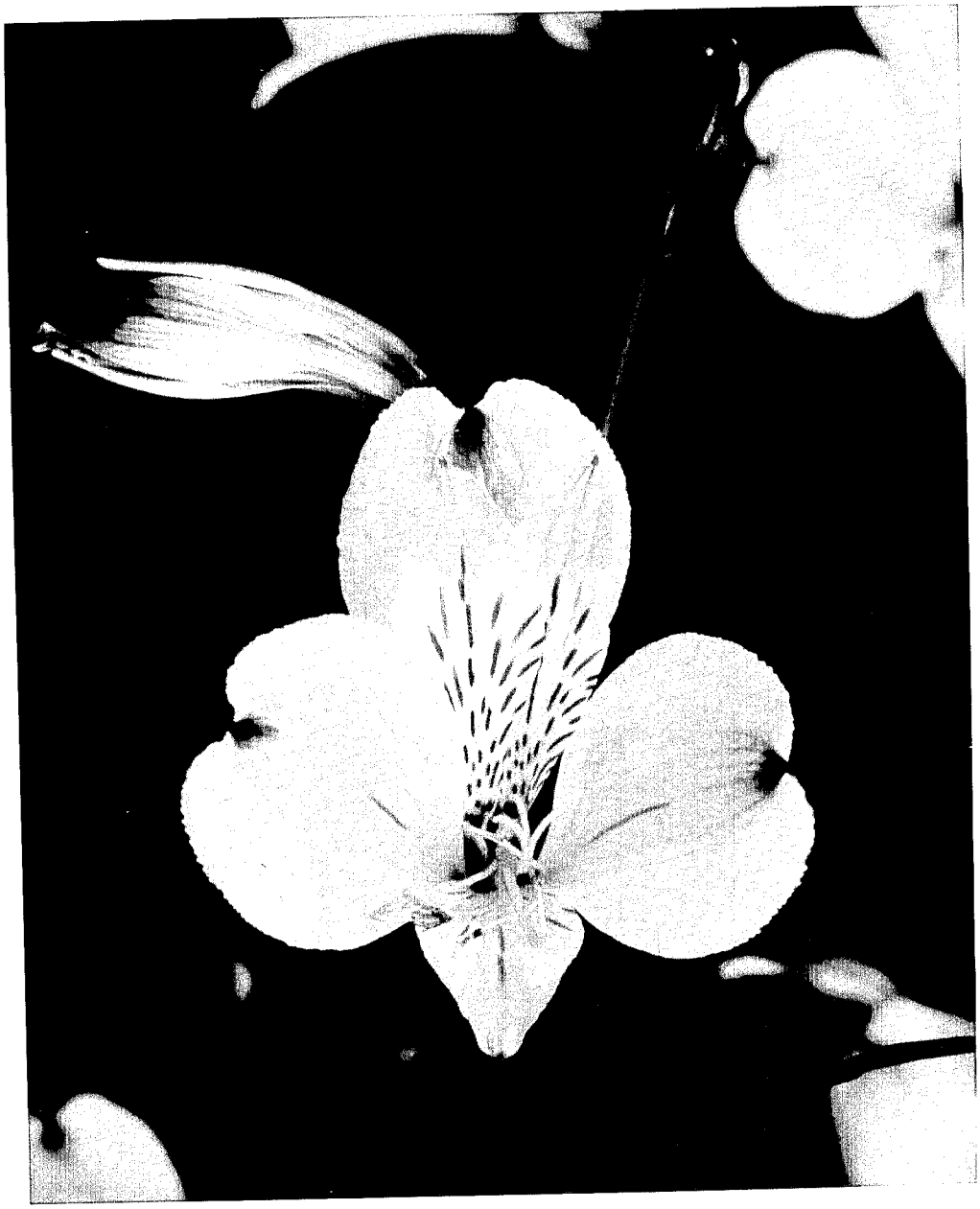

UNITED STATES PATENT AND TRADEMARK OFFICE

CERTIFICATE OF CORRECTION

PATENT NO. : Plant 8,204

DATED : April 13, 1993

INVENTOR(S) : G.E. Veldhuyzen Van Zanten

It is certified that error appears in the above-identified patent and that said Letters Patent is hereby corrected as shown below:

Column 1, line 13, delete"alstroemeria" and add "Alstroemeria"

Signed and Sealed this

Thirty-first Day of October 1995

*Attest:*

Bruce Lehman

BRUCE LEHMAN

*Attesting Officer*

*Commissioner of Patents and Trademarks*